(12) United States Patent
Haggiag et al.

(10) Patent No.: US 7,824,670 B2
(45) Date of Patent: Nov. 2, 2010

(54) USE OF IL6R/IL6 CHIMERA IN NERVE CELL REGENERATION

(75) Inventors: Shalom Haggiag, Rehovot (IL); Michel Revel, Rehovot (IL); Judith Chebath, Rehovot (IL); Alon Levy, Ramat Hasharon (IL); Peilin Zhang, Rehovot (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 810 days.

(21) Appl. No.: 10/498,899

(22) PCT Filed: Dec. 31, 2002

(86) PCT No.: PCT/IL02/01058
§ 371 (c)(1),
(2), (4) Date: May 16, 2005

(87) PCT Pub. No.: WO03/059376
PCT Pub. Date: Jul. 24, 2003

(65) Prior Publication Data
US 2005/0220761 A1    Oct. 6, 2005

(30) Foreign Application Priority Data
Dec. 31, 2001    (IL) ..................................... 147412

(51) Int. Cl.
*A61K 38/20*    (2006.01)
*A61K 35/30*    (2006.01)
(52) U.S. Cl. ........................................ 424/93.7; 514/12
(58) Field of Classification Search ................... None
See application file for complete search history.

(56) References Cited

U.S. PATENT DOCUMENTS 6,749,850 B1 * 6/2004 Finkelstein et al. ......... 424/93.7
7,201,896 B1 * 4/2007 Revel et al. ................. 424/85.2

FOREIGN PATENT DOCUMENTS

| JP | 09-087198 A | 3/1997 |
| JP | 2001-509371 A | 7/2001 |
| WO | WO 00 78331 A | 12/2000 |
| WO | WO 02 22149 A | 3/2002 |

OTHER PUBLICATIONS

Diaz Brinton R and Yamazaki RS. Advances and challenges in the prevention and treatment of Alzheimer's disease. Pharm Res. 1998; 15(3):386-398.*
Feign A and Zgaljardic D. Recent advances in Huntington's disease: implications for experimental therapeutics. Curr Opin Neurol. 2002; 15:483-489.*
Pincus DW et al. Neural stem and progenitor cells: A strategy for gene therapy and brain repair. Neurosurgery, 1998; 42(4):858-867. Downloaded from Neurosurgery Online, downloaded pages numbered as pp. 1-16 provided.*
Steece-Collier K et al. Etiology of Parkinson's disease: Genetics and enviornment revisted. Proc Natl Acad Sci, USA. 99(22):13972-13974.*
Lim 2002 Brain Research Bulletin 57(6):759-764.*
Kozorovitskiy 2003 Journal of Clincal and Experimental Neuropsychology 25(5):721-732.*
Alberts 1994. Molecular Biology of the Cell, pp. 104-111.*
Gutekunst 2000 (Current Opinion in Neurology 13:445-450).*
Lorincz 2009 (Molecular and Cellular Neuroscience 40:1-13).*
Le Belle 2002 (BioDrugs 16(6):389-401).*
Sutcliffe 2002 Nature Reviews Neuroscience 3:339-349.*
Haggiag Shalom et al "Induction of myelin gene expression in Schwann cell cultures by an interleukin-6 receptor-interleukin-6 chimera" FEBS Letters (1999) Vol. 457, pp. 200-204.
Pia Marz et al "Role of Interleukin-6 and Solule IL-6 Receptor in Region-Specific Induction of Astrocytic Differentiation and Neurotrophin Expression", Glia, 1999; 26:191-200.
Rolmola Davenport "Glutamate Receptors in Plants" Annals of Botany (2002) vol. 90 pp. 549-557.
Takizawa T et al "Directly linked soluble IL-6 receptor-IL-6 fusion protein induces astrocyte differentiation from neuroepithelial cells via activation of STAT3" Cytokine, (Mar. 2001) vol. 13, No. 5 pp. 272-279.
Watanabe et al., Characteristic localization of gp130 (the signal-transducing receptor component used in common for IL-6/IL-11/CNTF/LIF/OSM) in the rat brain, European Journal of Neuroscience, 8:1630-1640 (1996).
Ha et al., Localization of gp130 in the developing and adult mouse cerebellum, Journal of Chemical Neuroanatomy, 19:129-141 (2000).
Mizuno et al., Localization of molecules involved in cytokine receptor signaling in the rat trigeminal ganglion, Molecular Brain Research, 11:163-166 (1997).

* cited by examiner

*Primary Examiner*—Daniel E Kolker
(74) *Attorney, Agent, or Firm*—Browdy and Neimark, PLLC

(57) ABSTRACT

The present invention provides for the use of IL6R/IL6 chimera for the manufacture of medicaments for the treatment of neurological diseases and disorders.

6 Claims, 7 Drawing Sheets

NT　　　　　　　　　　　　　rhIL6/RIL6

BMP-2　　　　　　　　　　　Heregulin

| Marker of neurons | Marker of neural crest-derived progenitors | Marker of neurons |
|---|---|---|
|  |  |  |

Phase contrast of the above fields

|  |  |  |
|---|---|---|

NT BMP-2 rhIL6/RIL6

USE OF IL6R/IL6 CHIMERA IN NERVE CELL REGENERATION

FIELD OF THE INVENTION

The present invention provides for the use of IL6R/IL6 chimera for the manufacture of medicaments for the treatment of neurological diseases and disorders.

BACKGROUND OF THE INVENTION

The nervous system consists of two major portions: the central nervous system (CNS) and the peripheral nervous system (PNS). The CNS includes the brain and the spinal cord, and the PNS consists of all of the nerve tissue outside the CNS. The brain consists of the nervous tissue contained within the skull. The PNS is organized into nerves, bundles of nervous tissue that emanate from the CNS and extend throughout the body, where they provide pathways for signals travelling to and from the CNS portions (Encyclopaedia of human biology, volume 5 Ed Dulbecco).

The autonomic nervous system is that part of the PNS that regulates unconscious involuntary activities, such as the control of heart beat, movements of the digestive system, or glandular activities. It consists primarily of visceral efferent neurons that carry motor impulses to cardiac muscle, certain glands, and smooth muscles in blood vessels and organs of the thoracic and abdominal cavities.

The autonomic nervous system has two distinct anatomic and functional subdivisions: sympathetic and parasympathetic. The sympathetic neurons emerge from thoracic and lumbar regions of the spine, innervates smooth muscles of the arteries. Just as arteries penetrate all parts of the body, so do sympathetic fibres. The general effect of the sympathetic nervous system is to prepare the body for action in stressful situations.

The other division, the parasympathetic, or craniosacral, system, functions as the principal nerve supply to certain structures in the head. The parasympathetic system stimulates activities of the digestive organs and glands and slows the heartbeat and the respiratory rates. It tends to calm the body after a stress-producing experience, and it promotes activities that maintain life-support system.

The term "regeneration" generally stand for the ability of an organism to replace lost tissue. For example after surgical removal of a hepatic lobe, functioning new liver tissue is produced. In contrast, the nervous system usually does not form new nerve cells (neurons) after injury and therefore does not replace lost tissue. Recovery of lost function in the nervous system, when it occurs, is mediated by limited regenerative process. After section of a bundle of nerve fibres, axons may re-grow from surviving neuronal cell bodies, and eventually appropriate connections with other neurons are reformed. Successful regeneration is generally encountered if a nerve bundle is severed in the PNS. This is in sharp contrast with the course of events after lesions within the CNS. On damage to the brain or spinal cord of warm-blooded vertebrates, recovery of function is extremely limited.

Nerve growth factor (NGF) is a neurotrophic protein i.e. a special protein that controls the maintenance, size, extension of processes and transmitter synthesis in selected neurons of the PNS and CNS. Since the discovery of NGF, some 40 years ago, it provided the first evidence that nerve cells depend on specific extrinsic factors for their survival and function. Deficits of endogenous NGF or other neurothrophic factors may underlie or aggravate certain human neurodegenerative disorders, as well as apparent inability of injured adult CNS neurons to regenerate. New techniques made possible the discovery of other NGF-related trophic factors, these factors termed neutrophins (NTFs) include brain-derived neutrotrophic factor (BDNF), neurotrophins-3 (NT-3), neurotrophin 4/5 (NT-4/5), and neurotrophin-6 (NT-6). Also other neurotrophic factors unrelated to NTFs were discovered: such as insulin-like growth factors 1 and 2 (IGF-1, IGF-2), fibroblast growth factors (FGFs) and another neutrotrophic factor family, which includes ciliary neurotrophic factor (CNTF), leukaemia-inhibiting factor (LIF), interleukin-6 (IL-6), oncostatin M and Cardiotropin-1 (CT-1) (Reviewed in Elsvier's Encyclopedya of neuroscience eds Adelman at al. 1999).

LIF, CNTF, CT-1, OSM, IL-6 and IL-11 are cytokines that use gp 130 in their respective receptor complexes as a signal-transducing component (Taga et al. 1989, Kishimoto et al. 1994, Stahl et al. 1994 and Taga et al. 1997). LIF, CNTF, CT-1 and OSM support survival of several types of neurons in vitro (Ernsberger et al. 1989, Martinou et al. 1992, Taga 1996 and Horton et al. 1998). They induce cholinergic properties in cultured autonomic neurons (Yamamori et al. 1989, Patterson 1994). CNTF induces differentiation of autonomic neurons (Ernsberger et al. 1989).

It has been suggested that IL-6 acts as a nerve survival factor. Hama et al. (1989) reported that IL-6 can act as a neurotrophic agent, independent of the action of NGF, supporting neuronal survival of cultured postnatal rat septal cholinergic neurons. It was shown that IL-6, in contrast to NGF, does not affect differentiation of cultured embryonic rat septal cholinergic neurons. Horton et al. (1998) showed evidences that differentiation of sensory neurons from progenitors cells of neural crest origin is promoted by LIF and that only later in development, IL-6 promotes the survival of cultured neurons. Kushima et al. (1992) reported that IL-6 supports the survival of septal cholinergic neurons obtained from 10-day-old rats. Il-6, however in contrast to NGF, did not induce the differentiation of embryonic rat septal cholinergic neurons.

A review of the effects of IL-6 on cells of the central and peripheral nervous system indicates that the cytokine may have protective effects on neuronal cells as well as participate in inflammatory neuro-degenerative processes (Gadient and Otten, 1996, Mendel et al, 1998). On glial cells, CNTF and LIF are much more active than IL-6 to stimulate astrocyte differentiation and there is no effect on myelin protein producing cells (Kahn and De Vellis, 1994). IL-6 was found to prevent glutamate-induced cell death in hippocampal (Yamada et al. 1994) as well as in striatal (Toulmond et al. 1992) neurons. The IL-6 mechanism of neuroprotection against toxicity elicited by N-methyl-D-aspartate (NMDA), the selective agonist for NMDA subtype of glutamate receptors, is still unknown. In fact IL-6 was found to enhance the NMDA-mediated intracellular calcium elevation. In transgenic mice expressing higher levels of both IL-6 and soluble IL-6R (sIL6-R), an accelerated nerve regeneration was observed following injury of the hypoglossal nerve as shown by retrograde labeling of the hypoglossal nuclei in the brain (Hirota et al, 1996). In that work, the addition of IL-6 and sIL-6R to cultures of dorsal root ganglia (DRG) cells showed increased neurite extension in neurons, but no effect on myelinating cells or nerve generation from stem cells was reported.

Marz et al. (1998) show that in the PC-12 cell line (Greene et al. 1976), which is a tumor-derived line from a transplantable rat pheochromocytoma (vascular tumor of chromaffin tissue of the adrenal medulla or sympathetic paraganglia), only the combination of IL-6R and IL-6 but not IL-6 alone induces neuron specific differentiation. This result is not in line with the fact that these cells do express the IL-6 receptor.

As mentioned above, CNTF and LIF are cytokines acting through a common receptor system which comprises the LIF receptor (LIFR) and the gp130 chain, the latter being also part of the Interleukin-6 (IL-6) receptor complex (Ip et al, 1992). CNTF and LIF are, therefore, part of the IL-6 family of cytokines. In the case of CNTF and LIF, signal transduction operates through dimerization of LIFR with gp130, whereas in the case of IL-6 the signal is generated by the dimerization of two gp130 chains (Murakami et al, 1993). In order to bind gp130, IL-6 complexes with an IL-6 Receptor chain, which exists on certain cells as a gp80 transmembrane protein, but whose soluble form can also function as an IL-6R agonist when provided from outside the cell (Taga et al, 1989, Novick et al, 1992). By fusing the entire coding regions of the cDNAs encoding the soluble IL-6 receptor (sIL-6R) and IL-6, a recombinant IL6R/IL6 chimera can be produced in CHO cells (Chebath et al, 1997, WO99/02552). This IL6R/IL6 chimera has enhanced IL-6-type biological activities and it binds with a much higher efficiency to the gp130 chain in vitro than does the mixture of IL-6 with sIL-6R (Kollet et al, 1999).

The involvement of IL6R/IL6 in the differentiation of myelinating cells was first observed and studied in a melanoma cell line F10.9, where IL6R/IL6 chimera treatment caused transdifferentiation into myelinating Schwann cells (Chebath et al. 1997). This process involved growth arrest, loss of melanin synthesis and increase in glial cell markers. IL6R/IL6 chimera has been recently shown to induce myelinating genes e.g. MBP and P0, in embryonic Schwann cells (SC) precursors and in various tumor cells of neural crest origin (Chebath et al. 1997, Haggiag, et al. 1999, Haggiag et al, J. Neurosci. Res. 2001).

It has been observed that embryonic rat DRG explants cultured in the presence of IL6R/IL6 chimera form foci of cells with characteristic multipolar (stellar) dendritic extensions, as seen in Schwann cells or oligodendrocytes. These Schwann cell-like cells were isolated and their growth was found to be dependent on IL6R/IL6. Subclones of these cells were prepared and named CH cells (Haggiag et al. 1999). The CH cells are populations of Schwann cell precursors, which can differentiate into two directions: either myelinating Schwann cells or smooth muscle cells. When maintained without IL6R/IL6, cells of CH cell clone 1D11 have a flat morphology and slow growth, and stain for Smooth Muscle Actin (SMA). In contrast, when the CH cells are treated by IL6R/IL6, most cells differentiate into the Schwann cell phenotype and SMA is not expressed anymore. Upon treatment of CH cells with IL6R/IL6, the expression of myelin gene P0 and MBP are induced, and Pax-3 expression is repressed, indicating differentiation toward myelinating SC. When CH cells or SC are co-cultured with mouse neurons purified from DRGs, IL6R/IL6 promotes the binding of these cells along the axons, and the synthesis of P0 myelin protein (Haggiag et al, J. Neurosci. Res. 2001).

Application PCT/IL00/00363 relates to the use of IL6R/IL6 chimera for the manufacture of a medicament to generate myelinating cells or to stimulate, enhance or acceleration of myelinating cells and to induce, enhance, prolong or accelerate neuroprotection and to reduce or decelerate neuronal death.

Cells isolated from embryonic E10.5 rat neural tubes have been shown to undergo multiple rounds of self-renewing divisions in culture, and differentiate into neurons, Schwann cells, and smooth muscle-like myofibroblasts (Shah et al 1996). These cells have been termed neural crest stem cells (NCSCs). Cells with similar properties were isolated from uncultured E14.5 fetal rat sciatic nerve, using specific cell surface antibodies (Morrison et all 999). Such sciatic nerve-derived NCSCs (sNCSCs) are multipotent and self renew both in vivo and in vitro. They respond appropriately to instructive differentiation signals such as bone morphogenetic protein-2 (BMP2) and glial growth factor-2 (GGF2)/neuregulin-1 (Nrg1) (Shagh et al. 1994, 1996, 1997 and Morrison et al. 1999). These data suggest that multipotent, self renewing stem cells migrate from the neural crest of the neural tubes to peripheral tissues and continue to self renew in the peripheral tissues late into gestation.

The potential of post migratory sNCSCs isolated from rat fetal sciatic nerve was studied by direct transplantation in vivo into chick embryos (White et al. 2001). Bone morphogenetic protein-2 (BMP2) induces differentiation of sNCSCs into nerve cells and it is suggested that the choice of differentiation of these cells to either sympathetic or parasympathetic fates may be determined by the local concentration of this factor.

Autonomic neurons, Schwann (glial) cells and smooth muscle develop from the neural crest cells (Stemple et al. 1992). Three growth factors are known to promote differentiation along each of these three lineages, respectively: bone morphogenetic protein 2 (BMP2), glial growth factor 2 [GGF2, a neuregulin], and transforming growth factor β1 (TGF-β1) (Shah et al 1994 and 1996). Clonal analysis and serial observation of identified cells has suggested that each of these factors acts instructively rather than selectively on NCSCs [although some of the factors may do both (Dong et al. 1995)] i.e. GGF2, BMP2, and TGF-β1 individually direct the differentiation rather than the survival or proliferation of the majority of individual identified NCSCs plated at clonal density. The neural crest thus represents one of the few systems in which instructive lineage determination signals for multipotential stem cells have been identified (Morrison et al 1997).

Experiments have been performed in which NCSCs are exposed to different combinations of instructive signals. Depending upon the specific combination and concentration of signals tested, the experiments showed that either (i) the influence of one signal could dominate over others or (ii) the signals could exert equivalent influences, producing a mixture of lineage-committed progeny. These data therefore suggest that stem cell fate is not solely determined by what factors are present in the environment but is also influenced by cell-intrinsic differences in the relative sensitivity and timing of responses to different environmental signals (Shah et al. 1997).

Neural stem cells exist not only in the developing mammalian (embryonic) nervous system but also in the adult nervous system of all mammalian organisms, including humans. Dividing cells in the adult mouse subventricular zone (SVZ) continuously self-renew and give rise to progenies that migrate to the olfactory cortex, where they differentiate into astrocytes, oligodendrocytes and neurons (Altman et al. 1966 and Lois et al. 1994).

The function of these stem cells in the adult nervous system is uncertain. One possibility is that they are vestiges of evolution from more primitive organisms or an alternative view is that the adult mammalian nervous system retains a limited capacity for self-renewal that is important for its normal functions, like learning and memory. It is possible that the local generation of new neurons in structures could participate in the formation or integration of new memories. The ability of adult neurogenesis to be regulated by changes in the environment further supports a role in normal behavior. The implications would be that the brain controls behavior and behavior can change the structure of the brain (Gage et al. 2000).

Patent application WO0066188 discloses xenotransplant of choroid plexus cells from a neonatal mammal to provide a steady state supply of trophic factors for administration to a central nervous system in need of treatment for a neurological disease. The choroid plexus is well-innervated vascular tissue (more correctly an organ) covered with a basement membrane comprising the usual variants of collagen, one or more types of laminin proteoglycans and other extracellular matrix molecules, which is in turn covered by a unicellular epithelium-like layer and occurring in several consistent sites within the cerebral 230 ventricles. It appears to act as the source of most of the cerebrospinal fluid.

WO0066188 discloses a pharmaceutical composition, comprising an implant for implantation into the brain of a recipient mammal suffering from neurological disease, wherein the implant comprises living cells, derived from epithelial cells of the choroids plexus of another mammal, and the living cells are capable of expressing at least one product having a beneficial effect on the neurological disease into the brain of the recipient mammal. This patent specification describes the supply of neurothrophic factors from the implant to prevent deficits of endogenous NGF or other neurothrophic factors, which may underlie or aggravate certain human neurodegenerative disorders, as well as apparent inability of injured adult CNS neurons to regenerate.

Thus there exists a need to provide a therapeutic composition allowing nerve replacement in patients suffering from a neurological disease.

SUMMARY OF THE INVENTION

The present invention relates to the use of an IL6R/IL6 chimera, a mutein, fused protein, functional derivative, active fraction, circularly permutated derivative or salt thereof in the manufacture of a medicament for inducing neuron generation, wherein progenitor cells of embryonic, neonatal or adult origin are treated with IL6R/IL6 chimera in-vivo, or ex-vivo and thereafter transplanted to a patient.

The present invention provides the use of an IL6R/IL6 chimera, a mutein, fused protein, functional derivative, active fraction, circularly permutated derivative or salt thereof, in the manufacture of a medicament for inducing neuron generation e.g. in patients suffering from loss or atrophy of neurons caused inter alia by aging or by a neurological disease.

Furthermore, the invention provides the use of a cell expressing an IL6R/IL6 chimera, a mutein, fused protein, functional derivative, active fraction thereof, or an expression vector, preferably a lentiviral vector, comprising the coding sequence of an IL6R/IL6 chimera, a mutein, fused protein, active fraction thereof in the manufacture of a medicament for inducing neuron generation.

In one embodiment, the medicament of the invention may further comprise glial cells and/or a neurotrophic factor and/or a cytokine such as NGF, NTFs, BDNF, IGFs, FGFs, CNTF, LIF, G-CSF, OSM, IL-11, BMP-2, GGF-2, Nrg1 and TGF.

The invention also provides methods for regeneration of nerve cells in injured central nervous system comprising: administrating a therapeutically effective amount of an IL6R/IL6 chimera, a mutein, fused protein, functional derivative, active fraction, circularly permutated derivative or salt thereof, or a vector encoding an IL6R/IL6, a mutein, fused protein or an active fraction thereof, or a cell expressing an IL6R/IL6, a mutein, fused protein or an active fraction thereof, for restoring nerve cells to injured central nervous system (CNS). Preferably, along with the IL6R/IL6 chimera a neural progenitor cell or embryonic stem cell more preferably pre-stimulated with IL6R/IL6 chimera and with neurotrophic factor and/or cytokines such as NGF, NTFs, BDNF, IGFs, FGFs, CNTF, LIF, G-CSF, OSM, IL-11, BMP-2, GGF-2, Nrg1 and TGF is administrated. The methods provided by the present invention may be aimed for the treatment of patients suffering from a neurological disease e.g. Alzheimer's disease, Parkinson's disease, multiple sclerosis and Huntington's chorea patients or patients suffering from neurological diseases caused by a stroke, anoxia/asphyxia, physical injury, exposure to toxins and neoplastic disease.

In another aspect, the invention provides a method for rejuvenation comprising the administration of a therapeutically effective amount of IL6R/IL6 chimera, a mutein, fused protein, functional derivative, active fraction, circularly permutated derivative or salt thereof, or a vector encoding an IL6R/IL6, a mutein, fused protein or an active fraction thereof, for restoring nerve cells to injured central nervous system (CNS) preferably comprising a neural progenitor cell more preferably pre-stimulated with IL6R/IL6 chimera and with neurotrophic factor and/or cytokines such as NGF, NTFs, BDNF, IGFs, FGFs, CNTF, LIF, G-CSF, OSM, IL-11, BMP-2, GGF-2, Nrg1 and TGF.

The invention provides also a method for nerve regeneration in injured central nervous system (CNS) comprising stimulating a neural progenitor cell, in-vivo or preferably ex-vivo, prior to or during transplantation, with a composition comprising IL6R/IL6 chimera a mutein, a derivative or fragment thereof. Optionally, IL6R/IL6 may be supplied to the progenitor cells by co-transplantation of the progenitor cells with cells expressing IL6R/IL6 chimera or with an expression vector encoding the IL6R/IL6 chimera. According to the invention the progenitor cells may be derived from embryonic neonatal or adult origin and may be co-transplanted with glial cell, and/or with neurotrophic factor and or a cytokine such as NGF, NTFs, BDNF, IGFs, FGFs, CNTF, LIF, G-CSF, OSM, IL-11, BMP-2, GGF-2, Nrg1 and TGF.

The invention provides a method for nerve regeneration in injured central nervous system (CNS) comprising administration of IL6R/IL6 chimera, a mutein, fused protein, functional derivative, active fraction, circularly permutated derivative or salt thereof, or a vector encoding an IL6R/IL6, a mutein, fused protein or an active fraction thereof or cells expressing IL6R/IL6, a mutein, fused protein or an active fraction thereof to a patient suffering of loss or atrophy of neurons, wherein the loss or atrophy of neurons can be caused by aging, a neurological disease and/or by physical damage.

DETAILED DESCRIPTION OF THE INVENTION

Figure 1:
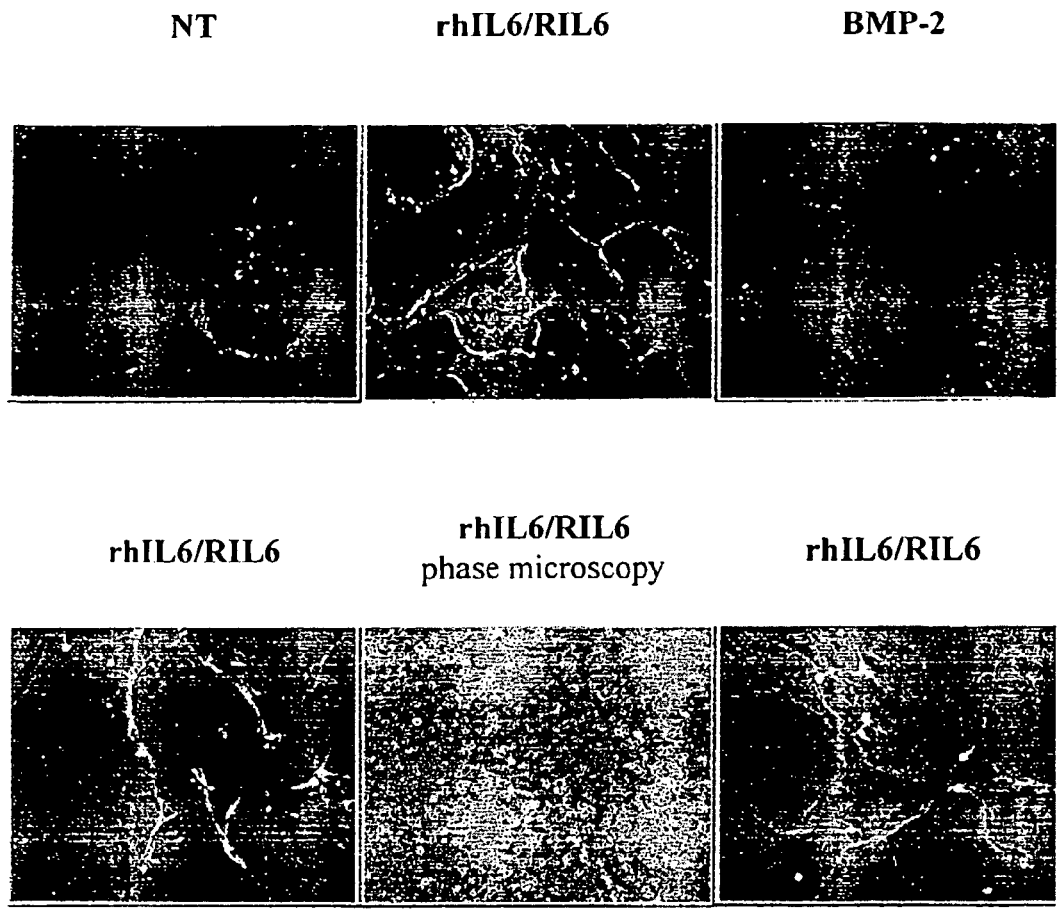
FIG. 1 shows DRG cultures from E14 rat embryos treated with IL6R/IL6 chimera. Dissociated DRG cells were first cultured for 4 days on glass coverslips coated (fibronectin-poly DL-lysine coated) in medium comprising DMEM/F12 (1:1) with 1% chick embryo extract, bFGF 20 ng/ml, 1% N2 supplement (Gibco), 2% B27 supplement (Gibco), 50 μM mercaptoethanol, 35 mg/ml (110 nM) retinoic acid (Morrison et al, 1997). At this point, some cultures were supplemented with pure rhIL6/RIL6 chimera produced in CHO cells (200 ng/ml; 2.3 nM), others left untreated (NT), or supplemented with BMP-2 (2 nM). After 9 days (day 13 from the beginning of culture) the DRG cells were fixed, subjected to fluorescent imunostaining for the neuron-specific beta III tubulin marker and photographed under UV light. Upper row, from left to right: Untreated (NT), with IL6RIL6, with BMP-2. Magnification 50×. Lower row, from left to right: all with IL6RIL6, the middle panel shows phase microscopy of the cells. Magnification 100×.

The invention relates to pharmaceutical compositions comprising IL6/IL6R chimera for regenerating neural cells in injured central nervous system (CNS). A pharmaceutical composition comprising IL6/IL6R chimera can also be used as a rejuvenation treatment.

The invention is based on the finding that the administration of an IL6R/IL6 chimera to normal neural stem cells, especially to neural crest cells, leads to nerve generation. Treating CNS injury with IL6/IL6R according to the invention has two important advantages: First, concomitantly with nerve cell generation, it also induces Schwann cell generation. Schwann cells are needed for myelination of both, the new nerve cells generated, as well as of adult damaged nerve cells. Second, in contrast to IL-6, the IL6/IL6R chimera acts in cells that lack the IL-6 receptor (gp-80) but have the GP130 receptor.

CNS injuries can be caused by neurological diseases.

A "neurological disease" is related to disorders of the central nervous system. It may for example be a general neurodegenerative disease, such as ageing, vascular disease, Alzheimer's disease, Parkinson's disease, or the autoimmune disease, multiple sclerosis (MS), it may be a result of an injury, such as a stroke, anoxia/asphyxia, or physical injury, such as from a blow to the head, it may be a result of exposure to local (e.g. meningitis) or systemic toxins, and it may be neoplastic. It may be genetically based, such as Huntington's chorea, or a disorder of metabolism such as lysosomal storage disease. There is a group of "general neurodegenerative diseases" including AZ and others, affecting the elderly, the usual pattern of response to acute injury (such as ischaemia), affecting any age group including stroke victims and car accident victims, autoimmune diseases such as MS, PD, and certain diseases, including deficiencies of metabolism, of neonates and foetuses.

"Restorative effect" is meant to include any beneficial modification of the disease process, including palliative, restorative, or proliferative effects acting on neural tissue.

"Rejuvenation" is meant to include attempts to reverse changes in a brain commonly caused by ageing, such as loss of volume, loss or atrophy of neurones, loss of memory, and loss of ability to cope with complex sensory inputs.

Rejuvenation also comprises restorative effects on existing neurones.

One aspect of the invention relates to a method for treating injuries to the central nervous system; the method comprising the step of administrating a pharmaceutical composition comprising IL6R/IL6 chimera to subjects in need. Optionally, the pharmaceutical composition may also comprise living cells.

In another aspect this invention relates to a method for causing at least partial rejuvenation of the brain of a mammal by treatment with IL6R/IL6 chimera with or without nerve stem cells as described below, wherein the method may employ implantation of an implant of cells derived from, embryonic or neonatal mammal or adult neural stem cells into the brain.

The term "regeneration" generally means the ability of an organism to replace lost tissue. For example after surgical removal of a hepatic lobe, functioning new liver tissue is produced.

In accordance with the invention, dorsal root ganglia (DRG) cells were extracted from Lewis rat E14 embryos essentially as described previously (Kleitman et al. 1991 and Haggiag et al. 1999) and cultured 4 days on flasks at 37° C. 5% $CO_2$ in medium comprising DMEM/F12 (1:1) with 1% chick embryo extract, bFGF 20 ng/ml, 1% N2 supplement (Gibco), 2% B27 supplement (Gibco), 50 μM mercaptoethanol, 35 mg/ml (110 nM) retinoic acid (Morrison et al, 1997). At this point, some cultures were supplemented with pure rhIL6/RIL6 chimera produced in CHO cells (200 ng/ml; 2.3 nM), others left untreated (NT), or supplemented with Bone Morphogenic Factor (BMP-2, 2 nM) or remaine untreated. After 9 days (day 13 from the beginning of culture) the cultured cells showed dense axonal network developed only after the treatment with IL6R/IL6 suggesting that IL6R/IL6 induces normal embryonic DRG cells to differentiate into neural cells. These results were confirmed by using a more homogeneous cell population, devoid of nerve cells, comprising mainly neural crest progenitor cells. IL6R/IL6 chimera acted as a nerve generative factor, and not as a survival factor, as evidenced by the fact that neuronal network can observed even in these homogeneous neural crest populations which are devoid of nerve cells. According to the invention, it has been also shown that in addition to nerve cells, glial cells were generated by treatment of neural crest enriched populations with the IL6R/IL6 chimera and that these glial cells are associated with the newly generated nerve cells present in the culture.

The effect of the IL6R/IL6 chimera on a population enriched with neural crest progenitor cells, was tested in parallel to the effect of BMP2 a factor, which is known to promote nerve differentiation. The results show that the nerve differentiation effect promoted by the IL6R/IL6 chimera is superior to that of BMP2, and that only the former induces, in addition to nerve cells, Schwann cell generation. Non-treated cells (left without cytokines) show only few, poorly developed neurons seen at 12 days and these neurons are not associated with glial cells.

The homogeneous population used to demonstrate the nerve generation properties of IL6R/IL6 chimera was obtained by sorting embryonic, DRG cells by fluorescent cytometry, for LNGFR positive cells. These cells were then cultured in defined serum free medium. The presence of nerve or glial cells was assessed by specific immunostaining techniques as described herein.

These results demonstrate that the IL6R/IL6 chimera can be used as a therapeutic agent for inducing nerve replacement in injured CNS. The IL6R/IL6 chimera may be administered locally, i.e. by direct injecting into the damaged area within the CNS. The chimera may induce nerve regeneration in stem cells localized within the CNS.

Neurotransplantation has been proposed as a potential treatment for the neurodegenerative disorders, which has no effective therapy (Gage et al. 1998 and Philpott L M et al. 1997). Therefore neural cell precursors, such as neural crest progenitor cells, can be co-implanted with IL6R/IL6 chimera or pre-treated with the IL6R/IL6 chimera prior to implantation to regenerate neurons in damage CNS. The implanted cells may be derived either from another mammal, from the same mammal, from a related compatible donor or from the same organism. Neural progenitor cells may be derived from the developing mammalian (embryonic) nervous system, from the neonatal nervous system or from the adult nervous system of mammalian organisms. In the present specification the terms neural progenitor cells and neural stem cells are interchangeable.

The implant may comprise in addition to neural stem cells other cells e.g. glial cells, known to support myelination and choroid plexus cells known to secrete neurotrophic factors.

The pharmaceutical composition may comprise in addition to IL6R/IL6 chimera other neurotrophic factors and cytokines such as NGF, NTFs, BDNF, IGFs, FGFs, CNTF, LIF, G-CSF, OSM, IL-11, BMP-2, GGF-2, Nrg1 and TGF.

The invention therefore relates to the use of an IL6R/IL6 chimera, a mutein, isoform, fused protein, functional derivative, active fraction, circularly permutated derivative or salt thereof for the manufacture of a medicament for the treatment of CNS injuries.

An "IL6R/IL6 chimera" (also called "IL6R/IL6" or "IL-6 chimera"), as used herein, is a chimeric molecule comprising a soluble part of the interleukin-6 receptor fused to all or a biologically active fraction of interleukin-6. The moieties of the chimeric protein can be fused directly, or they can be linked by any suitable linker, such as a disulfide bridge or a polypeptide linker. The linker may be a short linker peptide, which can be as short as 1 to 3 amino acid residues in length or longer, for example, 13 or 18 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met introduced between the amino acid sequence of the soluble IL-6 receptor and the IL-6 sequence. Examples of IL6R/IL6 chimeric molecules are known in the art and have been described in detail e.g. in WO 99/02552 or WO 97/32891.

The terms "treating" as used herein should be understood as preventing, inhibiting, attenuating, ameliorating or reversing any or all symptoms or cause(s) of neurodegenerative diseases or aging.

The invention provides for a new possibility of treating CNS injuries since IL6R/IL6 chimera exhibits a pronounced beneficial effect over BMP-2 in terms of neurogeneration and has also the capability of inducing myelinating cells and is able to act in the absence of IL-6 receptor.

As used herein the term "muteins" refers to analogs of an IL6R/IL6 chimera, in which one or more of the amino acid residues of the naturally occurring components of IL-6R/IL6 are replaced by different amino acid residues, or are deleted, or one or more amino acid residues are added to the original sequence of an IL6R/IL6, without changing considerably the activity of the resulting products as compared with the original IL6R/IL6. These muteins are prepared by known synthesis and/or by site-directed mutagenesis techniques, or any other known technique suitable therefore.

Muteins in accordance with the present invention include proteins encoded by a nucleic acid, such as DNA or RNA, which hybridizes to DNA or RNA, which encodes an IL6R/IL6, in accordance with the present invention, under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§63 and 6.4 (1987, 1992), and Sambrook et al. (Sambrook, J. C., Fritsch, E. F., and Maniatis, T. (1989) Molecular Cloning: A Laboratory Manual, Cold Spring Harbor Laboratory Press, Cold Spring Harbor, N.Y.).

Without limitation, examples of stringent conditions include washing conditions 12-20° C. below the calculated Tm of the hybrid under study in, e.g., 2×SSC and 05% SDS for 5 minutes, 2×SSC and 0.1% SDS for 15 minutes; 0.1×SSC and 0.5% SDS at 37° C. for 30-60 minutes and then, a 0.1× SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Any such mutein preferably has a sequence of amino acids sufficiently duplicative of that of an IL6R/IL6, such as to have substantially similar, or even better, activity to IL6R/IL6.

One characteristic activity of IL6R/IL6 is its capability of binding to gp130. An ELSA type assay for measuring the binding of IL6R/IL6 to gp130 has been described in detail in example 7 on page 39 of WO 99/02552, which is fully incorporated by reference herein. As long as the mutein has substantial binding activity to gp130, it can be considered to have substantially similar activity to IL6R/IL6. Thus, it can be determined whether any given mutein has at least substantially the same activity as IL6R/IL6 by means of routine experimentation comprising subjecting such a mutein, e.g., to a simple sandwich binding assay to determine whether or not it binds to an immobilized gp130, as described in example 7 of WO 99/02552.

In a preferred embodiment, any such mutein has at least 40% identity or homology with the amino acid sequence of IL6R/IL6 comprised in WO 99/02552. More preferably, it has at least 50%, at least 60%, at least 70%, at least 80% or, most preferably, at least 90% identity or homology thereto.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "percent identity" may be determined. In general, the two sequences to be compared are aligned to give a maximum correlation between the sequences. This may include inserting "gaps" in either one or both sequences, to enhance the degree of alignment. A percent identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at www.ncbi.nlm.nih.gov) and FASTA (Pearson W R, 1990; Pearson 1988).

Muteins of IL6R/IL6, which can be used in accordance with the present invention, or nucleic acid coding therefore, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of IL6R/IL6 may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table 1. More preferably, the synonymous amino acid groups are those defined in Table 2; and most preferably the synonymous amino acid groups are those defined in Table 3.

TABLE 1

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE 2

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |

TABLE 2-continued

More Preferred Groups of Synonymous Amino Acids

| Amino Acid | Synonymous Group |
|---|---|
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE 3

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Gys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of IL6R/IL6 polypeptides, for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

The term "fused protein" refers to a polypeptide comprising an IL6R/IL6, or a mutein or fragment thereof, fused with another protein, which, e.g., has an extended residence time in body fluids. An IL6R/IL6 may thus be fused to another protein, polypeptide or the like, e.g., an immunoglobulin or a fragment thereof.

"Functional derivatives" as used herein cover derivatives of IL6R/IL6, and their muteins and fused proteins, which may be prepared from the functional groups which occur as side chains on the residues or are additions to the N- or C-terminal groups, by means known in the art, and are included in the invention as long as they remain pharmaceutically acceptable, i.e. they do not destroy the activity of the protein which is substantially similar to the activity of IL6R/IL6, and do not confer toxic properties on compositions containing it.

These derivatives may, for example, include polyethylene glycol side-chains, which may mask antigenic sites and extend the residence of an IL6R/IL6 in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carboxylic aroyl groups) or O-acyl derivatives of free hydroxyl groups (for example that of seryl or threonyl residues) formed with acyl moieties.

An "active fraction" according to the present invention may e.g. be a fragment of IL6R/IL6. The term fragment refers to any subset of the molecule, that is, a shorter peptide that retains the desired biological activity. Fragments may readily be prepared by removing amino acids from either end of the IL6R/IL6 molecule and testing the resultant fragment for its properties to bind to gp130. Proteases for removing one amino acid at a time from either the N-terminal or the C-terminal of a polypeptide are known, and so determining fragments, which retain the desired biological activity, involves only routine experimentation.

As active fractions of an IL6R/IL6, muteins and fused proteins thereof, the present invention further covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to gp130.

The term "salts" herein refers to both salts of carboxyl groups and to acid addition salts of amino groups of the IL6R/IL6 molecule or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of IL6R/IL6, i.e., the ability to bind to gp130.

In a preferred embodiment of the invention, the IL6R/IL6 chimera is glycosylated at one or more sites.

A glycosylated form of an IL6R/IL6 chimera has been described in WO 99/02552 (PCT/IL98/00321), which is the chimeric molecule highly preferred according to the invention. The IL6R/IL6 chimera described therein is a recombinant glycoprotein, which was obtained fusing the entire coding sequence of the naturally occurring soluble IL-6 receptor δ-Val (Novick et al., 1990) to the entire coding sequence of mature naturally occurring IL-6, both from human origin.

The IL6R/IL6 chimera may be produced in any adequate eucaryotic or procaryotic cell type, like yeast cells, insect cells, bacteria, and the like. It is preferably produced in mammalian cells, most preferably in genetically engineered CHO cells as described in WO 99/02552. Whilst the protein from human origin is preferred, it will be appreciated by the person skilled in the art that a similar fusion protein of any other origin may be used according to the invention, as long as it retains the biological activity described herein.

The chimeric molecule can then be produced in bacterial cells, which are not capable of synthesizing glycosyl residues, but usually have a high yield of produced recombinant protein.

The IL6R/IL6 chimera may comprises an immunoglobulin fusion, i.e. the IL6R/IL6 according to the invention may be fused to all or a portion of an immunoglobulin. Methods for making immunoglobulin fusion proteins are well known in the art, such as the ones described in WO 01/03737, for example. The person skilled in the art will understand that the resulting fusion protein of the invention retains the biological activity of the IL6R/IL6 chimera. The resulting fusion protein ideally has improved properties, such as an extended residence time in body fluids (half-life), increased specific activity, increased expression level, or facilitated purification of the fusion protein.

The IL6R/IL6 chimera may be fused to the constant region of an Ig molecule. Preferably, to heavy chain regions, like the CH2 and CH3 domains of human IgG1, for example. Other isoforms of Ig molecules are also suitable for the generation of fusion proteins according to the present invention, such as isoforms $IgG_2$ or $IgG_4$, or other Ig classes, like IgM or IgA, for example. Fusion proteins may be monomeric or multimeric, hetero- or homomultimeric.

Functional derivatives of IL6R/IL6 chimera may be conjugated to polymers in order to improve the properties of the protein, such as the stability, half-life, bioavailability, tolerance by the human body, or immunogenicity.

Therefore, a preferred embodiment of the invention relates to a functional derivative of the IL6R/IL6 chimera comprising at least one moiety attached to one or more functional groups, which occur as one or more side chains on the amino acid residues.

A highly preferred embodiment relates to an IL6R/IL6 linked to Polyethlyenglycol (PEG). PEGylation may be carried out by known methods, such as the ones described in WO 92/13095, for example.

The IL6R/IL6 chimera may be delivered to the brain in any adequate formulation. It may also be delivered in form of cells expressing and/or secreting an IL6R/IL6 chimera, a mutein, fused protein, active fraction or circularly permutated derivative thereof.

The invention therefore further relates to the use of a neural stem cell and IL6R/IL6 chimera, a mutein, fused protein, active fraction or circularly permutated derivative thereof, for manufacture of a medicament for the treatment of CNS injuries. The cells may be administered in any suitable form. However, a polymer-encapsulated cell is a highly preferred mode of delivery of the cells. The encapsulation procedure is described in detail e.g. by Emerich et al (1994) or U.S. Pat. No. 5,853,385. Suitable cell lines and stable expression systems are well known in the art.

The delivery of IL6R/IL6 chimera to the brain may also be carried out using a vector comprising the coding sequence or an IL6R/IL6 chimera, a mutein, fused protein, active fraction or circularly permutated derivative thereof. The vector comprises all regulatory sequences needed for expression of the desired protein in the human body, preferably in the brain, more preferably in the striatum. Regulatory sequences for expression vectors are known by the person skilled in the art. The invention thus also relates to the use of a vector comprising the coding sequence of IL6R/IL6 chimera for manufacture of a medicament for the treatment of CNS injuries.

Any expression vector known in the art may be used according to the invention. However, a lentivirally-derived vector may be particularly useful for the delivery of IL6R/IL6 chimera directly into the striatum. Such lentiviral vectors are known in the art. They are specifically described e.g. in Kordower et al. (1999) or Déglon et al. (2000).

It is a further object of the present invention to provide a pharmaceutical composition comprising IL6R/IL6 chimera, a mutein, fused protein, functional derivative, active fraction, circularly permutated derivative or salt thereof, optionally together with one or more pharmaceutically acceptable carriers, diluents or excipients, for the treatment of CNS injury. The IL6/IL6 chimera used may be either from eukaryotic origin (glycosylated) or from bacterial origin (non-glycosylated).

The invention further relates to a pharmaceutical composition comprising IL6R/IL6 chimera, to a pharmaceutical composition comprising an expression vector, in particular a lentiviral gene therapy vector expressing IL6R/mL chimera and to pharmaceutical composition comprising in addition to the IL6R/IL6 chimera (in the form of protein or cells producing the chimera or an expression vector encoding the chimera) neural stem cells optionally together with one or more pharmaceutically acceptable carriers, diluents or excipients, for the treatment of CNS injury.

The definition of "pharmaceutically acceptable" is meant to encompass any carrier, which does not interfere with effectiveness of the biological activity of the active ingredient and that is not toxic to the host to which it is administered. For example, for parenteral administration, IL6R/IL6 chimera may be formulated in a unit dosage form for injection in vehicles such as saline, dextrose solution, serum albumin and Ringer's solution.

The IL6R/IL6 chimera can be administered to a patient in need of administration thereof in a variety of ways. The routes of administration include intracranial, intradermal, transdermal (e.g. in slow release formulations), intramuscular, intraperitoneal, intravenous, subcutaneous, oral, epidural, topical, and intranasal routes. Any other therapeutically efficacious route of administration can be used, for example by gene therapy wherein a DNA molecule encoding the IL6R/IL6 chimera is administered to the patient (e.g. via a vector), which causes the IL6R/IL6 chimera to be expressed and secreted in vivo. In addition the IL6R/IL6 chimera can be administered together with other components of biologically active agents such as pharmaceutically acceptable surfactants, excipients, carriers, diluents and vehicles.

A "therapeutically effective amount" is such that when administered, the MIFNAR2, or a functional derivative, analog, fusion protein or fragments thereof results in modulation of the biological activity of IFN-β. The dosage administered, as single or multiple doses, to an individual may vary depending upon a variety of factors, including the route of administration, patient conditions and characteristics (sex, age, body weight, health, size), extent of symptoms, concurrent treatments, frequency of treatment and the effect desired. Adjustment and manipulation of established dosage ranges are well within the ability of those skilled in the art, as well as in vitro and in vivo methods of determining the activity of MIFNAR2.

For parenteral (e.g. intravenous, subcutaneous, intramuscular) administration, IL6R/IL6 chimera can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

It is a further object of the present invention to provide for a method for treating CNS injury, comprising administering to a patient in need thereof an effective amount of IL6R/IL6 chimera, a mutein, fused protein, functional derivative, active fraction, circularly permutated derivative or salt thereof optionally together with a pharmaceutically acceptable carrier.

An "effective amount" refers to an amount of the active ingredients that is sufficient to affect the course and the severity of the diseases described above, leading to the reduction or remission of such pathology. The effective amount will depend on the route of administration and the condition of the patient.

The dosage administered, as single or multiple doses, to an individual will vary depending upon a variety of factor, including IL6R/IL6 chimera pharmacokinetic properties, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled.

A method for treating CNS injury, comprising administering to a patient in need thereof an effective amount of IL6R/IL6 chimera, a mutein, fused protein, active fraction or circularly permutated derivative thereof, or comprising administering to a patient in need thereof an expression vector comprising the coding sequence of IL6R/IL6 chimera, a mutein, fused protein, active fraction or circularly permutated derivative thereof, are further objects of the present invention and or neural stem cells.

It is a further object of the present invention to provide for a method for the preparation of differentiated nerve and associate glial cells for transplantation into patients in order to repair damage to nervous tissues. The IL6R/IL6 chimera will in this case be used ex-vivo to stimulate the development of neural cells from either embryonic neuro-glial progenitor cells or from human embryonic Stem cell lines (ES cells). Such stimulation can greatly improve the yield of nerve cells from in vitro cultures, facilitating the use of these tissues for subsequent transplantation.

The present invention will now be described in more detail in the following non-limiting examples and the accompanying drawings.

EXAMPLES

Example 1

The Effect of IL6RIL6 Chimera on Rat Embryonic Dorsal Root Ganglia (DRG) Cells.

The effect of IL6RIL6 chimera was tested on developing neuro-glial cells present in DRG at day 14 of embryonic development. DRG cells were prepared from Lewis rat E14 embryos as previously described (Kleitman et. 1991 and Haggiag et al, 1999). Dissociated DRG cells were first cultured for 4 days on glass coverslips (fibronectin-coated) in medium comprising DMEM/F12 (1:1) with 1% chick embryo extract, bFGF 20 ng/ml, 1% N2 supplement (Gibco), 2% B27 supplement (Gibco), 50 µM mercaptoethanol, 35 mg/ml (110 nM) retinoic acid (Morrison et al, 1997). At this point, some of the cultures were fixed (day 4) and other were supplemented with pure rhIL6/RIL6 chimera (produced in CHO cells as described in Chebath et al. 1997) and added at 200 ng/ml i.e. 23 nM. Other cultures were continued without addition (NT) or with 2 nM Bone Morphogenic Protein-2 (BMP-2). After 9 days (day 13 from beginning of culture) the DRG cells were fixed, subjected to fluorescent imunostaining for the neuron-specific beta III tubulin marker and photographed in the microscope under UV light. FIG. 1 shows very few undeveloped neurons in the cultures without addition, i.e. NT (upper row left), whereas in the cultures with IL6RIL6 (upper row middle and lower row right) many neuronal bodies are seen with developed axonal networks. Particularly interesting is the presence of primitive neurons (lower row, left) seen to proliferate and begin axon development. The cultures receiving BMP-2 (upper row, right) were not different from the NT cultures. In the cultures fixed at day 4 there were no visible neurons, demonstrating that IL6RIL6 induces a de novo differentiation of neurons.

Figure 2:
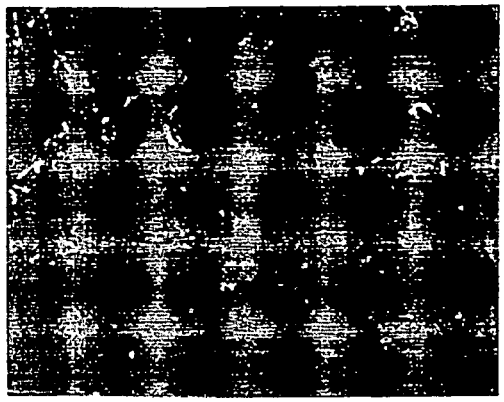
FIG. 2 shows DRG cultures from E14 rat embryos prepared and maintained as in FIG. 1. The cultures were supplemented from day 1 with either IL6RIL6 (200 ng/ml; 23 nM), or BMP-2 (2 nM) or Heregulin (300 ng/ml), or left untreated (NT). At day 12, the coverslip-attached cells were fixed and subjected to fluorescent immunostaining for the neural crest cell marker p75 LNGFR (Low affinity NGF Receptor). Upper left: NT. Upper right: with IL6RIL6. Lower left: BMP-2. Lower right: Heregulin. Note the cell elongation in the culture with IL6RIL6. Magnification 100×.
Figure 2:
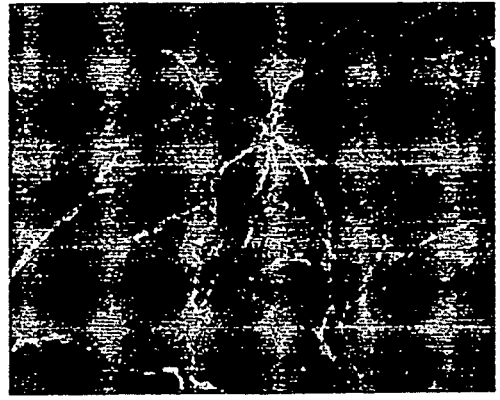
Figure 2:
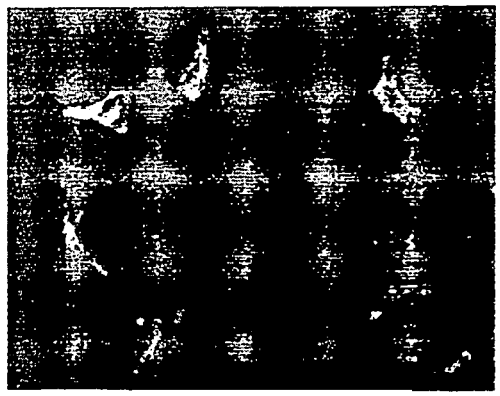
Figure 2:
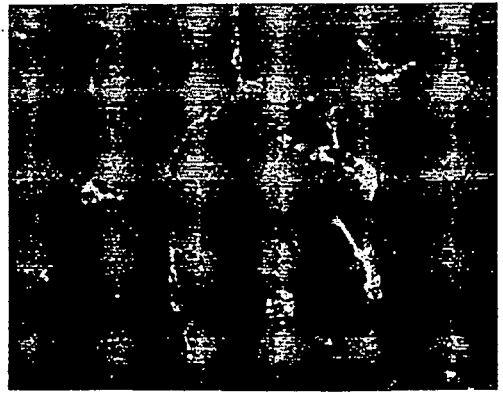

Similar cultures were immunostained for the p75 Low-affinity NGF Receptor (LNGFR), which is a marker of neural stem cells and early neuro-glial precursor cells. FIG. 2 shows the results after 12 days of cultures. Without addition (NT), groups of undifferentiated cells are stained (upper left), whereas with IL6RIL6 chimera the LNGFR-positive cells are elongated and form extended networks (upper right). In contrast, with BMP-2, groups of undifferentiated cells are seen (lower left). FIG. 2 (lower right) also shows cultures supplemented by another growth factor, Heregulin (300 ng/ml): most of the cells remained undifferentiated and only a few cells are seen elongating.

These results show that IL6RIL6 induces a pronounced differentiation of normal embryonic DRG cells into neural cells.

Example 2

The Effect of IL6RIL6 Chimera on Enriched Populations of Neural Crest Cells.

Figure 3:
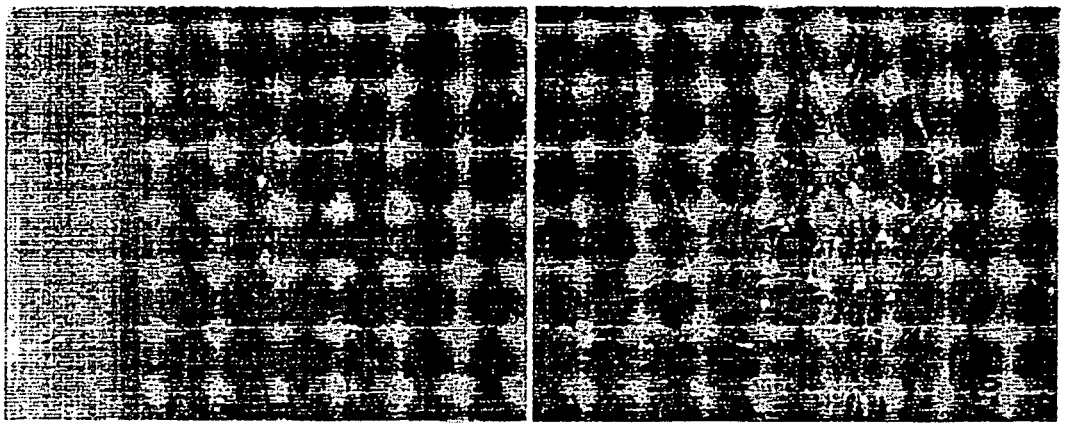
FIG. 3 shows an enriched population of neural crest-derived progenitor cells after culture for 12 days in the presence (+IL6RIL6) or absence (NT) of the IL6R/IL6 chimera. The enriched neural crest cells population was isolated by sorting rat E14 DRG cells for p75 LNGFR-positive cells (an early marker specifically present in neural crest-derived progenitor cells). These cells were then cultured as in FIG. 1, supplementing the cultures on day 1 with IL6RIL6 (200 ng/ml) or without addition. The coverslip-attached cells were immunostained for a marker of neurons and axons (neuron-specific beta III tubulin). Magnification 100×.

The DRG cell culture prepared as described in example 1, consists of a heterogeneous cell population comprising inter alia neural crest cells known to be the progenitors of different cell lineages such as neurons, glial cells and myofibroblasts. Neural crest cell give also rise to melanocytes in the ectoderm. IL6RIL6 chimera was tested in an enriched sub-population of undifferentiated neural crest progenitor cells, to check whether the molecule induces these precursor cells to differentiate into mature neurons. Such enriched neural crest progenitor cell sub-population was isolated by fluorescence activated cell sorting (FACS) of rat embryo E14 DRG cells for LNGFR-positive cells. This p75 Low-affinity NGF Receptor is a specific marker of neural crest cells and early neuro-glial progenitors, which is rather a neurotrophin receptor than an NGF receptor (indeed, when neurons differentiate they lose the p75 LNGFR and acquire the functional NGF receptor TrkA). The LNGFR$^+$-sorted cells were then cultured on glass coverslips as described in example 1. Some cultures were supplemented with 200 ng/ml IL6RIL6 and other left untreated. After 12 days, the fixed cells were subjected to fluorescent immunostaining for neuron-specific beta III tubulin. FIG. 3 shows that a population of enriched neural crest cell progenitors treated with IL6RIL6 differentiates and forms a dense neuronal network. Many neuron cell bodies were seen from which dense streams of axons developed. In contrast, in the absence of the cytokine only few, poorly developed neurons were observed. This was also observed in cultures with BMP-2 (not shown), contrasting with intense neuronal development in the IL6RIL6 treated cultures.

Figure 4:
FIG. 4 shows an enriched population of neural crest-derived progenitor cells (prepared as described in FIG. 3), cultured for 12 days with IL6RIL6 (as in FIG. 1) and subjected to fluorescence immunostaining either for a marker of neurons and axons (neuron-specific beta III tubulin) or for the marker of neural crest-derived progenitor cells (p75 LNGFR). The cells were observed by UV-microscopy in conditions where only immunostained cells are visible: upper row, left: stained for LNGFR (Magnification 100×); middle: stained for neuron-specific tubulin (different field, 100×); right: LNGFR (Magnification 300×). In the lower row the same fields (as in the upper row respectively) were observed under phase contrast to visualize all the cells.
Figure 4:
Figure 4:
Figure 4:
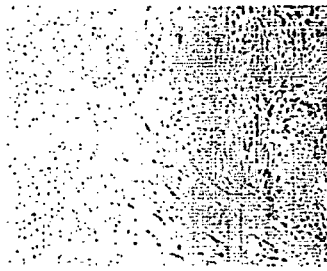
Figure 4:
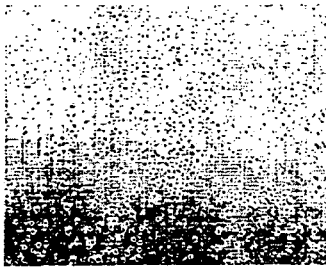
Figure 4:

Immunostaining with LNGFR demonstrated that the cells that formed elongated bundles in the IL6RIL6 treated cultures were indeed the LNGFR-positive cells, i.e. neural crest derived progenitor cells. FIG. 4 (left upper panel) shows that in the IL6RIL6 treated cultures, these LNGF-positive cells form elongated streams of aligned fibers, and in phase contrast (left lower panel) these streams are seen traversing many unstained cells. That these streams are formed by nerve axons is shown by immunostaining for neuron-specific tubulin, which reveals many axonal bundles (FIG. 4, middle panels). A higher magnification of the LNGFR-positive cells is shown in the upper right panel. Comparing to the phase contrast of the same field (lower right panel), shows axons that are in contacts with glial cells that have also differentiated from the LNGFR-positive neural crest progenitors. In the absence of IL6RIL6, the LNGFR-positive cells were more intensely stained and formed packed aggregates which in phase contrast corresponded to small and non elongated cells (not shown).

Figure 5:
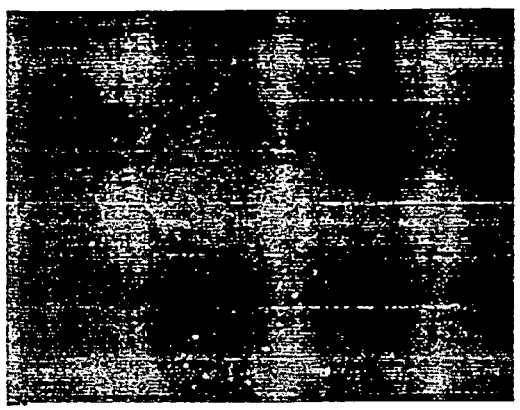
FIG. 5 shows the glial cells in an enriched population of neural crest-derived progenitor cells (prepared as described in FIG. 3) cultured for 8 days with IL6RIL6, or with BMP-2, or without addition (as described in FIG. 1). The fixed cultures were subjected to fluorescence immunostaining for the glial cell marker GFAP, and observed by UV-microscopy. Upper panels: compact colonies of GFAP-positive small glial cells are observed either with no treatment (left) or with BMP-2 (right). Lower panels: Cell cultures treated with IL6RIL6 exhibited a dramatic change, the glial cells being elongated and forming bundles of aligned cells.
Figure 5:
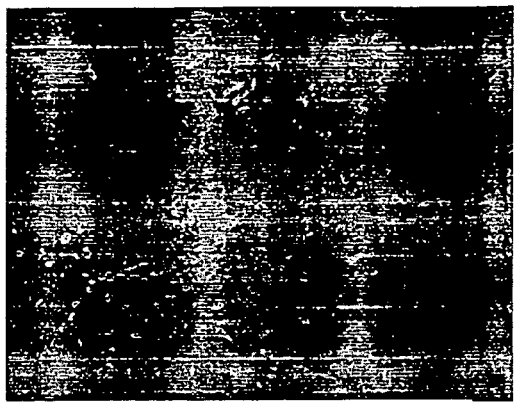
Figure 5:
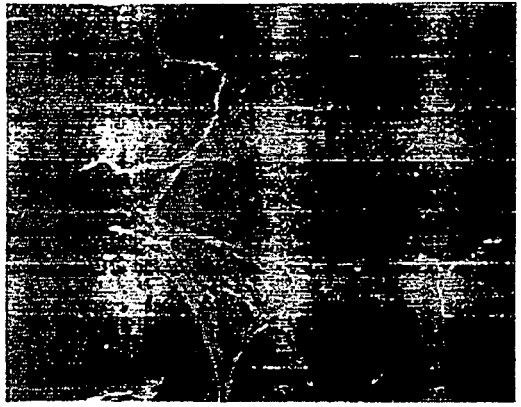
Figure 5:

Immunostaining for the glial marker GFAP was carried out on similar cultures of LNGFR-positive cells sorted by FACS from E14 DRG and cultured for 8 days with IL6RIL6 (200 ng/ml), or with BMP-2 (2 nM), or without addition (NT). FIG. 5 shows that in the untreated cultures (upper left) as well as with BMP-2 (upper right) the glial cells formed aggregates of small GFAP-positive cells. The cultures treated with IL6RIL6 exhibited a dramatic change in appearance of the glial cells, which were elongated and in bundles (lower two panels in FIG. 5). Using double staining (for both GFAP-positive glial cells and beta III tubulin-stained neurons), it could be observed that the glial cells were elongated along axon bundles forming in the IL6RIL6-treated cultures (not shown). This indicates that IL6RIL6 induces differentiation of both neurons and the glial cells which bind along neurons and differentiate into Schwann cells.

Figure 6:
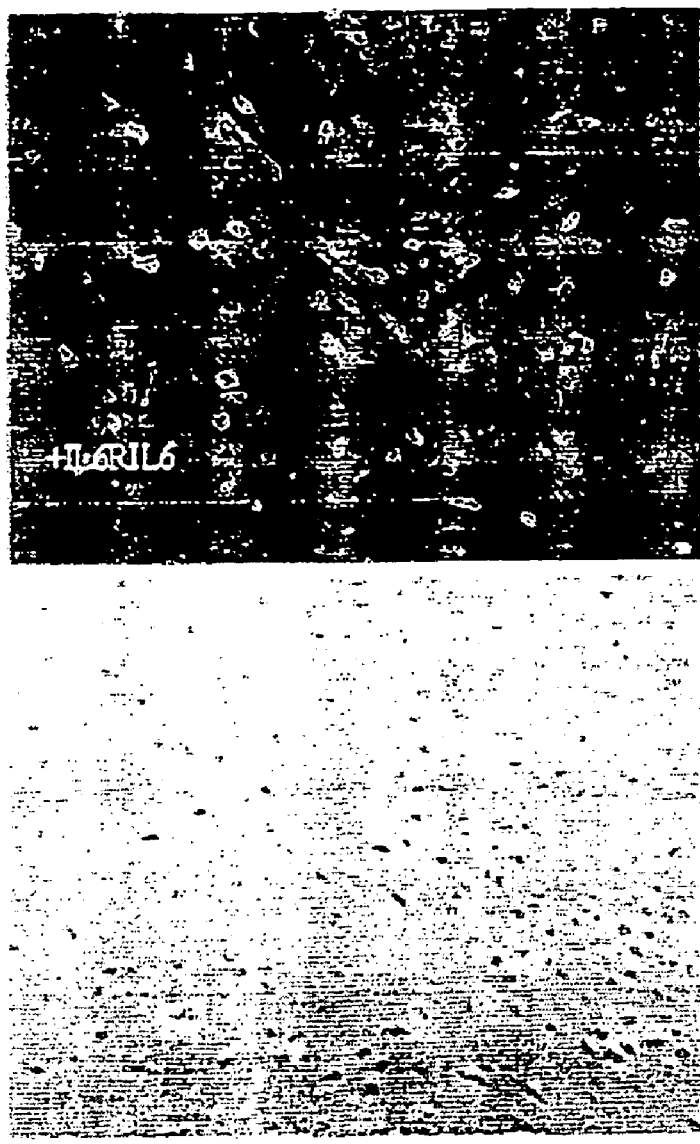
FIG. 6 shows glial cells having differentiated into myelinating Schwann cells from an enriched population of neural crest-derived progenitor cells (prepared as described in FIG. 3) cultured for 11 days with IL6RIL6 (200 ng/ml) under the conditions described in FIG. 1. The fixed cultures were subjected to fluorescence immunostaining for the transcription factor Krox-20, specific for myelinating Schwann cells. Lower panel: cells observed by phase contrast microscopy show a stream of elongated cells (of the type shown in FIG. 4 to contain axon fibers). Upper panel: cells observed by UV-microscopy show that the nucleus of many of the cells in the stream is positive for Krox-20, indicating their differentiation into myelinating Schwann cells, whereas few of the round undifferentiated cells outside the stream are positive.
Figure 7:
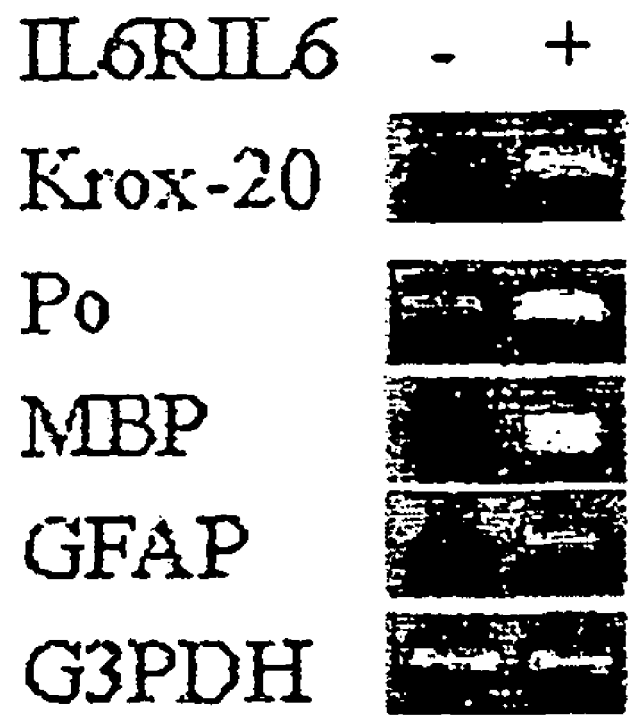
FIG. 7 shows measurements of mRNA induction for Krox-20, as well as for myelin components MBP and Po, in 6-days cultures of the LNGFR-sorted DRG cells in the presence or absence of IL6R/IL6 chimera by reverse-transcription and polymerase chain reaction (RT-PCR).

Immunostaining for the myelinating Schwann cells marker Krox-20 (a transcription factor required for myelin synthesis) was done on similar cultures of LNGFR-positive cells sorted by FACS from E14 DRG and cultured for 11 days with IL6RIL6 (200 ng/ml). FIG. 6 (lower panel, phase contrast) shows that the streams of fibers and elongated cells, shown above to be composed of differentiating axon bundles and glial cells, contain numerous Krox-20 positive Schwann cells (upper panel, UV light). Krox-20 is confined to the nucleus of the Schwann cells elongated along the axons. In the untreated cultures, neither the streams of axons and glial cells nor the appearance of strongly Krox-20-positive cells is observed (FIG. 7). Measurements by reverse-transcription and polymerase chain reaction (RT-PCR) demonstrated that IL6RIL6 induces the mRNAs for Krox-20, as well as for myelin components MBP and Po, in 6-days cultures of the LNGFR-sorted DRG cells (FIG. 7). The IL6RIL6 chimera causes, therefore, differentiation of neural crest progenitors (free of pre-existing differentiated neurons) into proto-endoneurium containing bundles of axons and their associated Schwann cells.

These results show that IL6R/IL6 induces differentiation on LNGFR-sorted cells, which elongate and form bundles, developing into neurons and Schwann cells. These results were obtained employing homogeneous cell populations, which are devoid of nerve cells, and comprise mainly neural crest cells and confirm the neurogenerative effect of IL6R/IL6 chimera found in example 1. Due to the fact that the experiments were carried out in the absence of preexisting nerve cells, it is concluded that the dense nerve network found by treating with the IL6R/IL6 chimera is due to a nerve generative activity, and not to a nerve survival activity. The results also show that in addition to the nerve cells, glial cells are generated by treatment with IL6R/IL6 chimera and that glial cell, more probably myelinating Schwann cells, are associated with nerve cells generated and may possibly myelinate these cells.

Thus, IL6R/IL6 chimera has a dual activity on normal nerve stem cells A—it promotes neurogeneration (which is stronger than that promoted by BMP-2) and B—it stimulates Schwann cells generation. This dual activity is fundamental for restoring nerve tissue and conferring neuroprotection.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning a range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Altman et al. 1966 J. Comp. Neurol. 126, 337-89.
Chebath et al. 1997 Eur Cytokine Netw (4):359-65.
Dong et al. 1995 Neuron 15, 585-96.
Ernsberger et al. 1989 Neuron 2:1275-1284.
Gadient et al. Brain Res. 1996 Jun. 10; 724(1):41-6.
Gage F. H. et al. (1998) Curr. Op. Neuro. 8, 671-676.
Gage et al. 2000 Science 287, 1433-8.
Greene et al. 1976 PNAS 73, 2424-8.
Haggiag et al. 1999 Febs Lett 457:200-204.
Haggiag et al 2001 J Neurosci Res. 2001 Jun. 15; 64(6):564-74.
Hama et al. Neurosci Lett 1989 Oct. 9; 104(3):340-4.
Hirota et al. J Exp Med. 1996 Jun. 1; 183(6):2627-34.
Horton et al. 1998 Eur J Neurosci 10:673-9.
Kishimoto et al. 1994 Cell 76:253-262.
Kahn et al. Glia. 1994 October; 12(2):87-98.
Kleitman et al. 1991 Tissue culture methods for the study of myelination MIT press p 337-377.ln: Banker et al. Eds.
Kollet et al. Blood. 1999 Aug. 1; 94(3):923-31.
Kushima et al. Prog Neuropsychopharmacol Biol Psychiatry. 1992 September; 16(5):617-33.
Lois et al 1994 Science 264, 1145-8.
Martinou et al. 1992 Neuron 8:737-44.
Marz et al. 1998 European Journal of Neuroscience 10 2765-73.
Mendel et al. Eur J Immunol. 1998 May; 28(5):1727-37.
Morrison et al. 1997 Cell 88, 287-98.
Novick et al. Cytokine. 1992 January; 4(1):6-11.
Patterson 1994 PNAS 91:7833-5.
Shah et al. 1994 Cell 77, 349-360.
Shah et al. 1996 Cell 85, 331-343.
Shah et al. 1997 PNAS 94, 11369-74.
Stahl et al. 1994 J Neurobiol 25:1454-66.
Stemple et al. 1992 Cell 71, 973-85.
Taga et al. 1989 Cell 58:573-581.
Taga et al 1992 PNAS 89:10998-11001.
Taga 1996 J Neurochem 67:1-10.
Taga et al. 1997 Annu Rev Immunol 15:797-819.
Toulmond et al. Neurosci Lett. 1992 Sep. 14; 144(1-2):49-52.
White et al. 2001 Neuron 29, 57-71.
Yamada et al. Brain Res. 1994 Apr. 18; 643(1-2):173-80.
Yamamori et al. 1989 Science 246:1412-6.

The invention claimed is:

1. A method of increasing the number of neurons in a patient, comprising stimulating neural progenitor cells by culturing the cells ex vivo with a composition comprising IL6R/IL6 chimera, fused protein, functional derivative, circularly permutated derivative or salt thereof prior to transplantation, and then subsequently transplanting the cells to a patient suffering from loss or atrophy of neurons caused by aging or by a neurological disease.

2. A method according to claim 1, wherein the progenitor cells are of embryonic origin.

3. A method according to claim 1, wherein the progenitor cells are of adult origin.

4. A method according to claim 1, wherein the progenitor cells are co-transplanted with glial cells.

5. A method according to claim 1, wherein the progenitor cells are co-transplanted with one or more neurotrophic factors or cytokines selected from the group consisting of NGF, NTFs, BDNFs, IGFs, FGFs, CNTF, LIF, G-CSF, OSM, IL-11, BMP-2, GGF-2, Nrg1 and TGF.

6. The method according to claim 1, wherein the neurological disease is selected from, Alzheimer's disease, Parkinson's disease, multiple sclerosis and Huntington's chorea.

* * * * *